(12) United States Patent
Liao et al.

(10) Patent No.: US 8,871,251 B2
(45) Date of Patent: Oct. 28, 2014

(54) LIPOSOME AND METHOD FOR PRODUCING THE SAME

(75) Inventors: Kuang-Wen Liao, Hsinchu (TW); Yen-Ku Liu, Taipei (TW); Yu-Ling Lin, Hualien County (TW); Ching-Yi Lin, Taipei County (TW)

(73) Assignee: Can Heal BioMediTech Corp., Tapei (TW)

( * ) Notice: Subject to any disclaimer, the term of this patent is extended or adjusted under 35 U.S.C. 154(b) by 866 days.

(21) Appl. No.: 12/545,060

(22) Filed: Aug. 20, 2009

(65) Prior Publication Data
US 2010/0119593 A1    May 13, 2010

(30) Foreign Application Priority Data
Nov. 11, 2008   (TW) ................................ 97143530 A

(51) Int. Cl.
*A61K 9/127* (2006.01)
*A61K 38/19* (2006.01)
*A61K 31/7088* (2006.01)

(52) U.S. Cl.
CPC ............ *A61K 31/7088* (2013.01); *A61K 38/191* (2013.01); *A61K 9/1278* (2013.01); *A61K 9/1272* (2013.01); *A61K 9/127* (2013.01)
USPC ........................................................ 424/450

(58) Field of Classification Search
USPC ........................................................ 424/450
See application file for complete search history.

(56) References Cited

U.S. PATENT DOCUMENTS

| 6,284,267 | B1 | 9/2001 | Aneja | |
| 2002/0058060 | A1* | 5/2002 | Kan et al. | 424/450 |
| 2003/0073619 | A1* | 4/2003 | Mahato et al. | 514/8 |
| 2005/0058603 | A1* | 3/2005 | Gao et al. | 424/9.32 |
| 2005/0123617 | A1* | 6/2005 | Chang et al. | 424/490 |
| 2007/0190107 | A1* | 8/2007 | Tosatti et al. | 424/423 |

FOREIGN PATENT DOCUMENTS

| CN | 1564680 | 1/2005 |
| CN | 1947702 | 4/2007 |
| TW | I226249 | 1/2005 |
| TW | I230616 | 4/2005 |
| WO | 2005/051351 | 6/2005 |
| WO | 2007/127272 | 11/2007 |

OTHER PUBLICATIONS

Article Titled "Lipid Encapsulation Enables the Effective Systemic Delivery of Polyplex Plasmid DNA" jointly authored by Heyes J. et al., in Molecular Therapy, vol. 15 No. 4, Apr. 2007, pp. 713-720.
Article Titled "Liposome-Encapsulated Curcumin in Vitro and In Vivo Effects on Proliferation, Apoptosis, Signaling, and Angiogenesis" jointly authored by Li et al., in American Cancer Society, pp. 1322-1331, published online Aug. 9, 2005 in Wiley InterScience.
Article Titled "Liposomal curcumin with and without oxaliplatin: effects on cell growth, apoptosis, and angiogenesis in colorectal cancer", jointly authored by Li et al., in Mol Cancer Ther Apr. 2007 pp. 1276-1282.
"Office Action of Taiwan Counterpart Application", issued on May 28, 2012, p. 1-p. 10, in which the listed references were cited.

\* cited by examiner

*Primary Examiner* — Kevin Hill
(74) *Attorney, Agent, or Firm* — Jianq Chyun IP Office

(57) ABSTRACT

A liposome including a neutral lipid membrane, a positively charged polymer, and a surface active polymer is provided. The neutral lipid membrane is formed as a hollow sphere, the positively charged polymer is dispersed on the neutral lipid membrane by non-covalent bonding, and the surface active polymer is dispersed on the neutral lipid membrane by non-covalent bonding. The liposome can stably adsorb various amounts of biomaterials by non-covalent bonding.

42 Claims, 10 Drawing Sheets

LIPOSOME AND METHOD FOR PRODUCING THE SAME

CROSS-REFERENCE TO RELATED APPLICATION

This application claims the priority benefit of Taiwan application serial no. 97143530, filed Nov. 11, 2008. The entirety of the above-mentioned patent application is hereby incorporated by reference herein and made a part of specification.

BACKGROUND OF THE INVENTION

1. Field of the Invention

The present invention generally relates to a liposome, in particular, to a liposome capable of stably adsorbing a material.

2. Description of Related Art

Liposome is a micro hollow sphere formed by lipid bilayer and has a structure similar to that of cell membrane. Particularly, the inner layer and the outer layer of the liposome are formed by the hydrophilic end of the lipid as hydrophilic aqueous phase systems, while the hydrophobic end of the lipid is aggregated into a lipophilic group, forming a surrounded structure between the inner layer and the outer layer.

The liposome has a structure similar to that of cell membrane and excellent biocompatibility and biodegradability, and is widely used in biological technology, such as transfection, drug delivery, vaccine, and gene therapy. That is to say, the materials, such as nucleic acid, protein, and drugs are encapsulated in the liposome, such that the materials enter an organism together with the liposome, so as to achieve the purpose of transfection and drug delivery. Generally, in order to improve the transfection efficiency of the liposome or the specificity of the drug delivery, the hydrophilic terminal functional group or the hydrophobic terminal functional group of the lipid of the liposome is modified by chemical bonding, to change the property of the liposome or to make the liposome to carry a targeting molecule. However, modifying the lipid of the liposome by chemical bonding has many disadvantages, for example, the formation of the chemical bonding needs a long reaction time, the chemical bonding may cause activity degradation of the protein bonded with the liposome, and the purification step of the liposome with chemical bonding gets complex. That is to say, modifying the functional group of the liposome by chemical bonding or making the liposome to carry a material may impact the property of the liposome or of the carried material.

SUMMARY OF THE INVENTION

Accordingly, the present invention is directed to a liposome, in which a positively charged polymer and a surface active polymer are dispersed on a neutral lipid membrane by non-covalent bonding.

The present invention is further directed to a method for producing a liposome, which is suitable for producing the liposome mentioned above.

The present invention provides a liposome, including a neutral lipid membrane, a positively charged polymer, and a surface active polymer. The neutral lipid membrane is formed as a hollow sphere, the positively charged polymer is dispersed on the neutral lipid membrane by non-covalent bonding, and the surface active polymer is dispersed on the neutral lipid membrane by non-covalent bonding.

The present invention further provides a method for producing a liposome including the following steps. First, a multi-layer neutral lipid membrane is formed in a vessel. Next, a solution of a positively charged polymer and a solution of a surface active polymer are added into the vessel. Then, the vessel is shaken.

In an embodiment of the present invention, the ratio of the neutral lipid membrane, the positively charged polymer, and the surface active polymer ranges from 5:2:2 to 60:1:1.

In an embodiment of the present invention, the ratio of the neutral lipid membrane, the positively charged polymer, and the surface active polymer ranges from 5:2:2 to 30:1:1.

In an embodiment of the present invention, the ratio of the neutral lipid membrane, the positively charged polymer, and the surface active polymer is 3:1:1.

In an embodiment of the present invention, the neutral lipid membrane is selected from a group consisting of DLPC, DOPC, DMPC, DPPC, DSPC, DOPC, DMPE, DPPE, DOPE, DMPA, DPPA, DOPA, DMPG, DPPG, DOPG, DMPS, DPPS, and DOPS.

In an embodiment of the present invention, the neutral lipid membrane includes DLPC and DOPC.

In an embodiment of the present invention, the positively charged polymer is selected from a group consisting of polyamine, polyethyleneimine (PEI), polyvinylpyrrolidone, and polylactic acid.

In an embodiment of the present invention, the positively charged polymer is PEI.

In an embodiment of the present invention, the surface active polymer is selected from a group consisting of crosslinked polyacrylate, saponin, and polyethylene glycol.

In an embodiment of the present invention, the surface active polymer is polyethylene glycol.

In an embodiment of the present invention, the non-covalent bonding includes hydrophilic and hydrophobic force, electrostatic force, hydrogen bond, and van der waals force.

In an embodiment of the present invention, the neutral lipid membrane is fluorescent.

In an embodiment of the present invention, the liposome encapsulates a biologically active material.

In an embodiment of the present invention, the biologically active material is selected from a group consisting of virus, protein, peptide, nucleic acid, polysaccharide, carbohydrate, lipid, glycoprotein, and pharmaceutical ingredients.

In an embodiment of the present invention, the liposome adsorbs a material by non-covalent bonding to form a liposome composition.

In an embodiment of the present invention, the force between the liposome and the material includes electrostatic force.

In an embodiment of the present invention, the material is protein.

In an embodiment of the present invention, the material is nucleic acid.

In an embodiment of the present invention, the material is deoxyribonucleic nucleic acid (DNA).

In an embodiment of the present invention, the material is ribonucleic acid (RNA).

In an embodiment of the present invention, the material is targeting molecule.

In an embodiment of the present invention, the material is antibody.

In an embodiment of the present invention, the material is cytokine.

In an embodiment of the present invention, the material is peptide.

In an embodiment of the present invention, the step of shaking the vessel makes the neutral lipid membrane formed as a hollow sphere, and the positively charged polymer and the surface active polymer dispersed on the neutral lipid membrane by non-covalent bonding.

In an embodiment of the present invention, the formation method of the neutral lipid membrane includes the following steps. First, a neutral lipid solution is added into a vessel. Next, the solvent in the neutral lipid solution is removed, to form a multi-layer neutral lipid membrane at the bottom of the vessel.

In an embodiment of the present invention, the method for producing a liposome further includes passing the formed liposome through a pore membrane.

In an embodiment of the present invention, the size of the pore membrane is 200 nm.

The positively charged polymer and the surface active polymer of the liposome of the present invention are dispersed on the neutral lipid membrane by non-covalent bonding. Moreover, the liposome can adsorb a material by non-covalent bonding to form a liposome composition.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Figure 1:
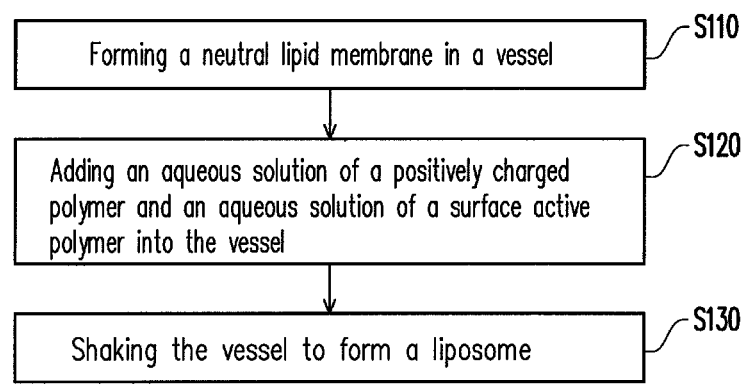
FIG. 1 is a process flow chart of a method for producing a liposome according to an embodiment of the present invention.

Reference will now be made in detail to the present embodiments of the invention, examples of which are illustrated in the accompanying drawings. Wherever possible, the same reference numbers are used in the drawings and the description to refer to the same or like parts.

FIG. 1 is a method for producing a liposome according to an embodiment of the present invention.

Referring to FIG. 1, first, Step S110 of forming a neutral lipid membrane in a vessel is performed. Particularly, in this embodiment, a neutral lipid solution is first added into a pear-shaped flask. Next, the solvent in the neutral lipid solution is removed by vacuum concentration, to form a multi-layer film-like neutral lipid membrane at the bottom of the pear-shaped flask. The neutral lipid membrane is selected from a group consisting of DLPC, DOPC, DMPC, DPPC, DSPC, DOPC, DMPE, DPPE, DOPE, DMPA, DPPA, DOPA, DMPG, DPPG, DOPG, DMPS, DPPS, and DOPS. In this embodiment, the neutral lipid membrane includes DLPC and DOPC. It should be noted that, in an embodiment, a fluorescent dye can be added into the neutral lipid solution, such that the formed neutral lipid membrane is fluorescent. Thus, the formed liposome is fluorescent.

Next, Step S120 of adding an aqueous solution of a positively charged polymer and an aqueous solution of a surface active polymer into the vessel is performed. The positively charged polymer is selected from a group consisting of polyamine, polyethyleneimine (PEI), polyvinylpyrrolidone, and polylactic acid. The surface active polymer is selected from a group consisting of crosslinked polyacrylate, saponin, and polyethylene glycol. In this embodiment, the positively charged polymer is PEI, and the surface active polymer is polyethylene glycol. The ratio of the neutral lipid membrane, the positively charged polymer, and the surface active polymer of the liposome ranges from 5:2:2 to 60:1:1, and preferably ranges from 5:2:2 to 30:1:1, and more preferably is 3:1:1.

Next, Step S130 of shaking the vessel is performed to form a liposome. Particularly, shaking the vessel will make the neutral lipid membrane formed as a hollow sphere due to hydration (swelling), and the positively charged polymer and the surface active polymer will be dispersed on the neutral lipid membrane by non-covalent bonding to form a liposome due to their hydrophobic nature and hydrophobic nature. The non-covalent bonding includes hydrophilic and hydrophobic force, electrostatic force, hydrogen bond, and van der waals force. It should be noted that, the formed liposome can be purified by centrifugation. Further, the formed liposome can be passed through a pore membrane to get the liposome with the desired size. In an embodiment, the size of the pore membrane is, for example, 200 nm.

Accordingly, the neutral lipid membrane, the positively charged polymer, and the surface active polymer will form a liposome at a special ratio, and the positively charged polymer and the surface active polymer are dispersed on the neutral lipid membrane by non-covalent bonding. That is to say, the positively charged polymer and the surface active polymer are embedded on the neutral lipid membrane due to their physical properties without using the chemical bonding. Therefore, the method for producing a liposome of this embodiment has the features of simplifying the process steps and shortening the process time.

The liposome formed by the above production method has the features of being capable of encapsulating a biologically active material and being capable of adsorbing a material. Hereinafter, the features and the application scope of the liposome are introduced.

Like commonly well-known liposomes, the liposome of the present invention can encapsulate a biologically active material. The biologically active material is, for example, selected from a group consisting of virus, protein, peptide, nucleic acid, polysaccharide, carbohydrate, lipid, glycoprotein, and pharmaceutical ingredients. Therefore, the liposome of the present invention can be applied in biological technology, such as transfection, drug delivery, vaccine, and gene therapy.

It should be noted that, the liposome of the present invention can adsorb a material by non-covalent bonding to form a liposome composition. Particularly, the liposome adsorbs the negatively charged part of the material by, for example, the positively charged polymer, such that the liposome adsorbs the material by means of electrostatic force. Besides, the liposome has a high capacity for the adsorbed material, the binding reaction time of the liposome and the material is short, and the adsorption force between the liposome and the material is stable. Further, like the liposome, the liposome composition has the property of being capable of being centrifuged, thus being capable of being isolated by centrifugation.

Hereinafter, the present invention is illustrated in detail with embodiments, such that those skilled in the art can implement the present invention, but the embodiments are not intended to limit the scope of the present invention.

In an embodiment, the adsorbed material can be a protein, that is, the liposome adsorbs a protein to form a liposome composition. Therefore, the liposome can be applied in experimental technology, such as protein quantitation and protein purification and isolation.

In an embodiment, the adsorbed material can be a nucleic acid, for example, deoxyribonucleic acid (DNA), ribonucleic acid (RNA), or other nucleic acids, that is, the liposome can bind with a nucleic acid into a liposome composition. Therefore, the property of the liposome of binding with nucleic acid can be applied in experimental technology, such as purification and isolation of nucleic acid.

In an embodiment, the adsorbed material can be a targeting molecule, for example, antibody, cytokine, peptide with specific sequence or nucleic acid with specific sequence, that is, the liposome can bind with a targeting molecule into a liposome composition. Thus, the liposome composition can be used as a probe to detect the existence of specific protein, nucleic acid, or cell. Further, when the liposome of the liposome composition is fluorescent, the fluorescence intensity emitted by the liposome composition can be used to detect and quantify a protein, nucleic acid, or cell, without additionally adding a fluorescent dye for labeling the targeting molecule, thus simplifying the analysis step.

In an embodiment, the liposome encapsulates a biologically active material, for example, selected from a group consisting of virus, protein, peptide, nucleic acid, polysaccharide, carbohydrate, lipid, glycoprotein, and pharmaceutical ingredients. Further, the adsorbed material is, for example, a targeting molecule, such as antibody, cytokine, peptide with specific sequence or nucleic acid with specific sequence. Thus, the liposome composition has cell specificity, tissue specificity, or tumor specificity. That is to say, the liposome composition can target a specific position of the cell or cell to be treated, so as to improve the transfection efficiency or the therapy effect of the liposome composition. Further, the specificity of the liposome composition can effectively eliminate the damage to normal tissue or cell, thus the liposome composition is an excellent drug carrier and gene carrier.

In the embodiments, the liposome adsorbs the material by non-covalent bonding, thus avoiding the influence or damage to the properties of the adsorbed material, such as activity or configuration. Further, the reaction time between the liposome and the adsorbed material is short and the adsorption force is stable, and the liposome has a high capacity for the adsorbed material, so the property of the liposome of adsorbing the adsorbed material can be applied in biological technology, such as purification, transfection, drug delivery, vaccine, and gene therapy.

Hereinafter, the capability of the liposome of the present invention to adsorb a material to form a liposome composition and the practical application of the liposome in biological detection, cell transfection, and drug delivery are experimentally demonstrated. The following description is to illustrate the present invention in detail, such that those skilled in the art can implement the present invention, but is not intended to limit the scope of the present invention.

In the following experimental examples, the liposome used includes DLPC and DOPC, PEI, and polyethylene glycol, and in Experimental Examples 1 to 6, Experimental Example 8, and Experimental Example 9, the ratio of DLPC and DOPC, PEI and polyethylene glycol is 3:1:1; in Experimental Example 7, the ratio of DLPC and DOPC, PEI and polyethylene glycol is 10:3:3 and 10:1:1.

EXPERIMENTAL EXAMPLE 1

Figure 2:
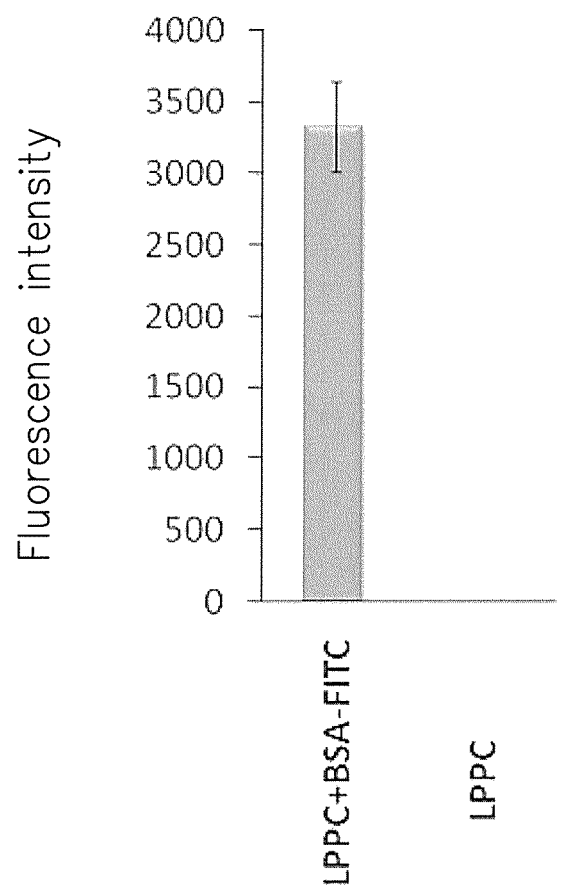
FIG. 2 shows experimental result of adsorbing bovine serum albumin with fluorescein isothiocyanate with a liposome.

In this experiment, whether the liposome can adsorb a protein is observed. First, bovine serum albumin with fluorescein isothiocyanate (BSA-FITC) was added into a liposome solution and reacted for 30 min. Next, the liposome solution was centrifuged at a speed of 10,000 rpm, and the supernatant was removed, to get a liposome composition (LPPC+BSA-FITC). The liposome composition was analyzed. The experimental result is as shown in FIG. 2. Referring to FIG. 2, the transverse axis in FIG. 2 represents the liposome composition (LPPC+BSA-FITC) and the liposome (LPPC), and the longitudinal axis represents the fluorescence intensity measured by a fluorescence spectroscopy. As shown in FIG. 2, the fluorescence intensity of the liposome composition (LPPC+BSA-FITC) is significantly greater than that of the liposome (LPPC), which indicates that the liposome composition contains the bovine serum albumin with fluorescein isothiocyanate (BSA-FITC). Therefore, it can be known from the experiment that, the liposome can adsorb protein to form a liposome composition.

EXPERIMENTAL EXAMPLE 2

Figure 3:
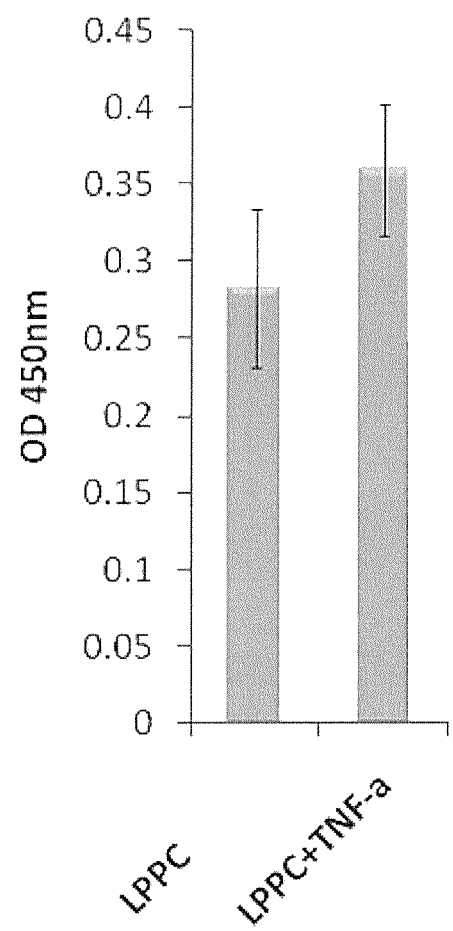
FIG. 3 shows experimental result of adsorbing tumor necrosis factor with a liposome.

In this experiment, whether the liposome can adsorb cytokine is observed. First, tumor necrosis factor-$\alpha$ (TNF-$\alpha$) was added into a liposome solution and reacted. Next, the liposome solution was centrifuged at a speed of 10,000 rpm, the liposome composition (LPPC+TNF-$\alpha$) after centrifugation was collected and reacted with anti-TNF-$\alpha$ antibody with HPR molecule for 1 h. Next, the liposome composition (LPPC+TNF-$\alpha$) was analyzed. The experimental result is as shown in FIG. 3. Referring to FIG. 3, the transverse axis in FIG. 3 represents the liposome composition (LPPC+TNF-$\alpha$) and the liposome (LPPC), and the longitudinal axis represents the absorbance measured by a spectrophotometer. As shown in FIG. 3, the absorbance of the liposome composition (LPPC+TNF-$\alpha$) is significantly greater than that of the liposome (LPPC), which indicates that the liposome composition contains the TNF-$\alpha$. Therefore, it can be known from the experiment that, the liposome can adsorb cytokine to form a liposome composition.

EXPERIMENTAL EXAMPLE 3

Figure 4:
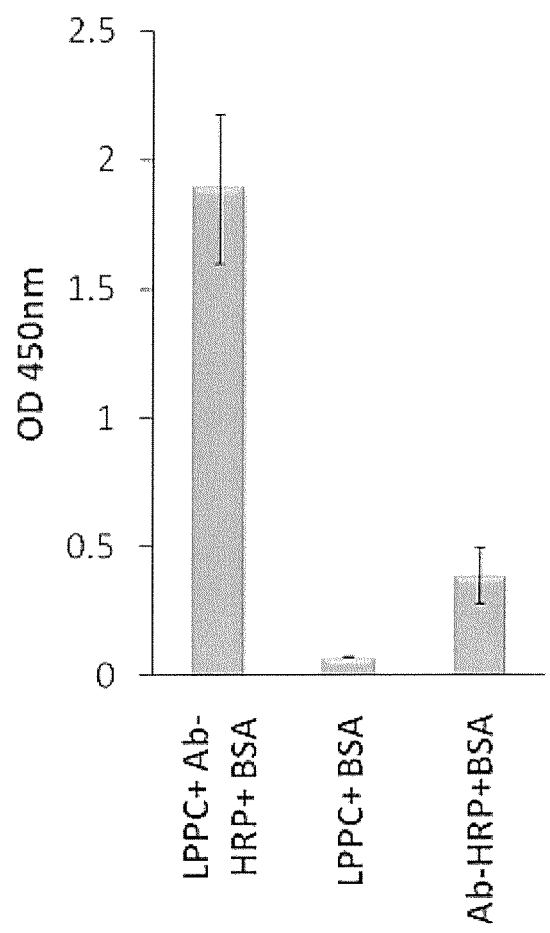
FIG. 4 shows experimental result of adsorbing rabbit anti-rat IgA monoclonal antibody with HPR molecule with a liposome.

In this experiment, whether the liposome can adsorb antibody is observed. First, rabbit anti-rat IgA monoclonal antibody with HPR molecule (Ab-HRP) was added into a liposome solution and reacted for 1 h. Next, the redundant positive charges were neutralized with excessive BSA, and then the liposome solution was centrifuged at a speed of 10,000 rpm. The liposome composition (LPPC+Ab-HRP+BSA) after centrifugation was collected and analyzed. The experimental result is as shown in FIG. 4. Referring to FIG. 4, the transverse axis in FIG. 4 represents the liposome composition (LPPC+Ab-HRP+BSA), the liposome (LPPC+BSA), and the rabbit anti-rat IgA monoclonal antibody with HPR molecule (Ab-HRP+BSA), and the longitudinal axis represents the absorbance measured by a fluorescence spectroscopy. As shown in FIG. 4, the absorbance of the liposome composition (LPPC+Ab-HRP+BSA) is significantly greater than that of the liposome (LPPC+BSA), which indicates that the liposome composition contains the rabbit anti-rat IgA monoclonal antibody. Therefore, it can be known from the experiment that, the liposome can adsorb antibody to form a liposome composition.

EXPERIMENTAL EXAMPLE 4

Figure 5:
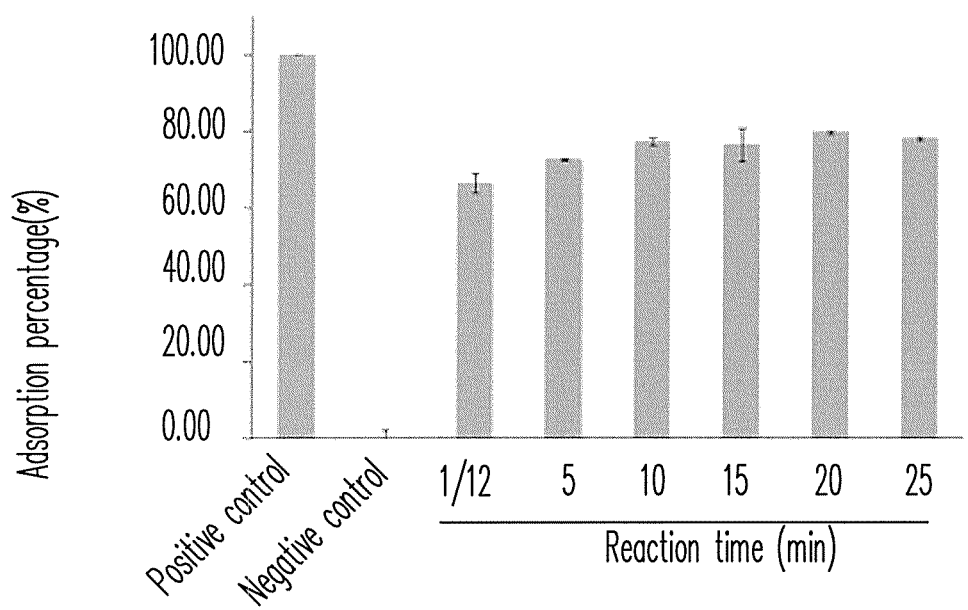
FIG. 5 shows experimental result of the degree of adsorption of a liposome to bovine serum albumin at different reaction times of the liposome and bovine serum albumin with fluorescent dye fluorescein isothiocyanate.

In this experiment, the reaction time of the liposome and bovine serum albumin for forming a liposome composition is observed. First, bovine serum albumin with fluorescent dye fluorescein isothiocyanate (BSA-FITC) was added into a liposome solution, and after different reaction times, the liposome solution was centrifuged at a speed of 10,000 rpm. The liposome composition (LPPC+BSA-FITC) was collected and analyzed by a spectrophotometer. The experimental result is as shown in FIG. 5. Referring to FIG. 5, the transverse axis in FIG. 5 represents the liposome composition (LPPC+BSA-FITC) formed at the reaction time of 5 s, 5 min, 10 min, 15 min, 20 min, 25 min, a positive control being a mixed solution of the liposome and bovine serum albumin without being centrifuged, a negative control being the liposome, and the longitudinal axis represents the degree of adsorption of the liposome to bovine serum albumin, in which the degree of adsorption of the liposome to bovine serum albumin is in direct ratio to the measured fluorescence intensity, and the fluorescence intensity measured with positive control is considered to be 100% of the degree of adsorption of the liposome. As shown in FIG. 5, a liposome composition is formed merely after mixing the liposome solution and bovine serum albumin for about 5 s, that is, the reaction time for forming the liposome composition from the liposome and bovine serum albumin is very short. Therefore, it can be known from the experiment that, the liposome has the property of rapidly adsorbing a charged material.

EXPERIMENTAL EXAMPLE 5

Figure 6:
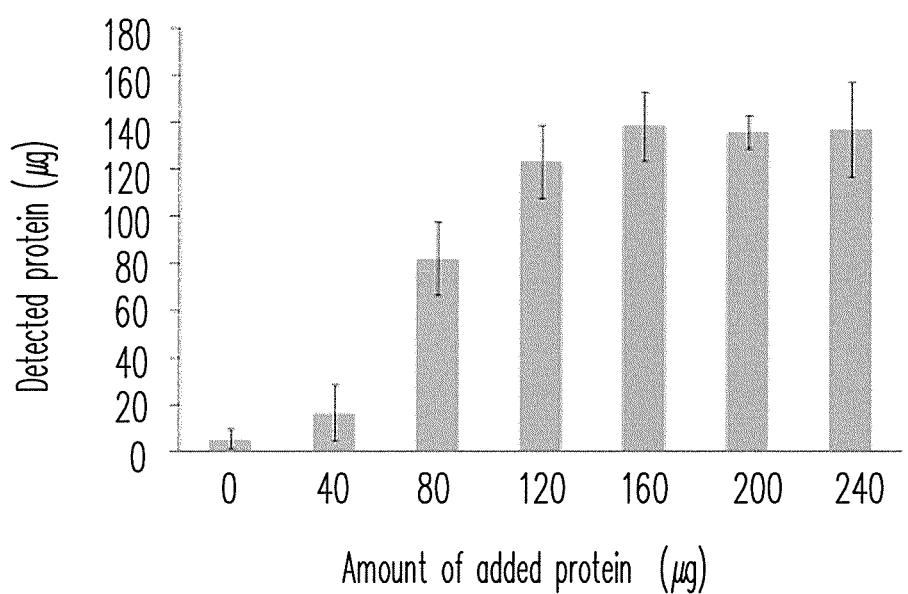
FIG. 6 shows experimental result of adsorbing different amounts of bovine serum albumin with a liposome.

In this experiment, the adsorption capacity of the liposome to bovine serum albumin is observed. First, different amounts of bovine serum albumin (BSA) were added into a liposome solution and reacted. Next, the liposome solution was centrifuged at a speed of 10,000 rpm, and the liposome composition (LPPC+BSA) was collected and the protein content in the liposome composition was quantified. The experimental result is as shown in FIG. 6. Referring to FIG. 6, the transverse axis in FIG. 6 represents the amount of bovine serum albumin added into the liposome solution, and the longitudinal axis represents the protein content detected on 40 µg liposome. As shown in FIG. 6, 40 µg liposome can adsorb about 140 µg bovine serum albumin, that is to say, the liposome has a high capacity for protein. Therefore, it can be known from the experiment that, the liposome has a high capacity to a charged material.

EXPERIMENTAL EXAMPLE 6

Figure 7:
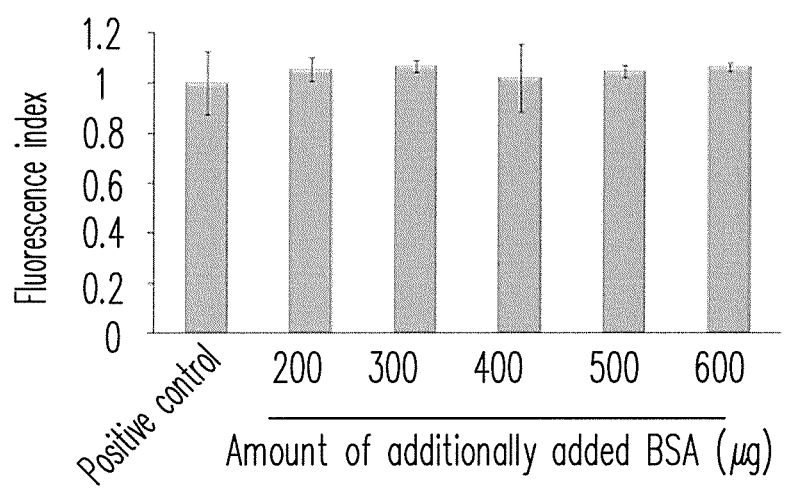
FIG. 7 shows experimental result of additionally adding different amounts of bovine serum albumin after a liposome and bovine serum albumin with fluorescent dye fluorescein isothiocyanate have interacted previously.

In this experiment, whether the adsorption force between the liposome and bovine serum albumin is stable is observed. First, 42 µg bovine serum albumin with fluorescent dye fluorescein isothiocyanate (FITC-BSA) was added into a liposome solution and reacted for 20 min, to form a liposome composition (LPPC+BSA-FITC). Next, different amounts of bovine serum albumin (BSA, without fluorescent dye fluorescein isothiocyanate) were additionally added, liposome solution was centrifuged at a speed of 10,000 rpm, and the liposome composition was collected and analyzed by a spectrophotometer. The experimental result is as shown in FIG. 7. Referring to FIG. 7, the transverse axis in FIG. 7 represents experimental groups with 200 µg, 300 µg, 400 µg, 500 µg, and 600 µg bovine serum albumin (BSA) additionally added into the liposome composition and a positive control without bovine serum albumin additionally added into the liposome composition, and the longitudinal axis represents the detected fluorescent index. As shown in FIG. 7, compared with the liposome composition without additionally adding bovine serum albumin, the addition of bovine serum albumin into the liposome composition has little impact on the fluorescent index of the liposome composition. That is, once the liposome has adsorbed protein, the adsorbed protein is not easily replaced by the subsequently added protein. That is to say, the liposome has stable adsorption force with a charged material.

EXPERIMENTAL EXAMPLE 7

Figure 8A:
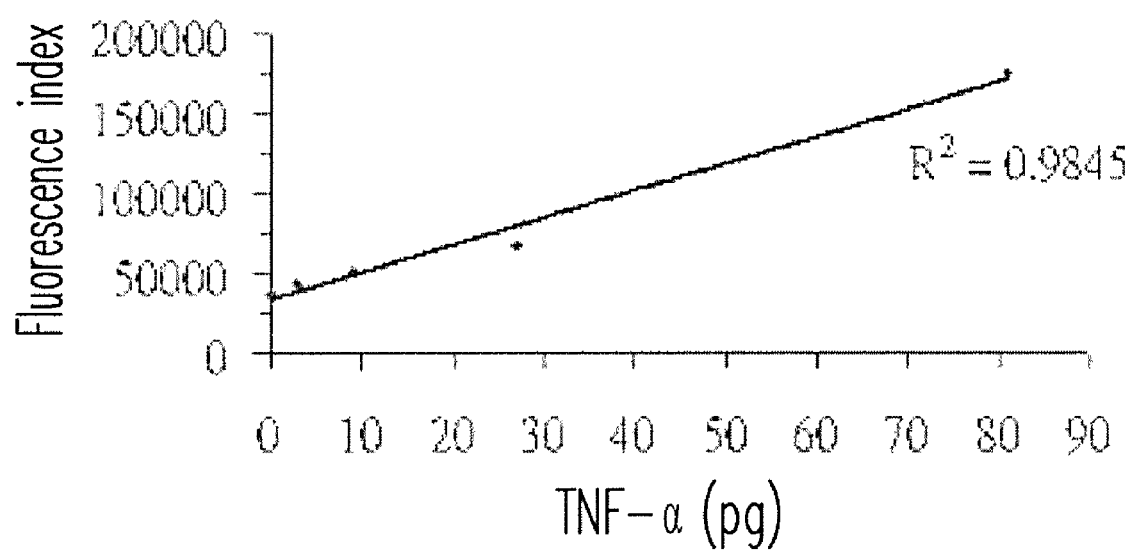
FIG. 8A shows experimental result of adsorbing different amounts of TNF-α with a liposome.
Figure 8B:
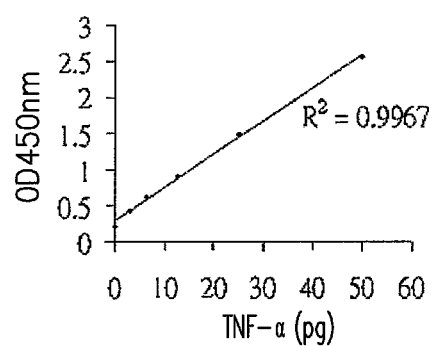
FIG. 8B shows experimental result of adsorbing different amounts of TNF-α with a commercial fluorescence immunoassay kit.

In this experiment, whether the adsorption capability of the liposome to protein can be applied in detection of protein concentration is observed. The experiment flow of evaluating the adsorption capability of the liposome to protein is as follows. First, different amounts of TNF-α was added into 1 µl liposome solution and reacted at room temperature for 20 min. Next, 5 µg BSA was added and a blocking step was performed at room temperature for 20 min. Next, a primary antibody was added and reacted for 60 min and a secondary antibody was added and reacted for 30 min in sequence, and then the fluorescence intensity of the liposome was detected by a flow cytometer. The experimental result is as shown in FIG. 8A, and the transverse axis in FIG. 8A represents the amount of added TNF-α, and the longitudinal axis represents the detected fluorescence intensity. The control experiment uses a commercial fluorescence immunoassay kit to detect the protein concentration, and the experiment flow is as follows. First, capture antibody was coated on a detection plate overnight. Next, a blocking step was performed at room temperature for 60 min. Next, TNF-α was added and reacted at room temperature for 60 min. Then, a primary antibody was added and reacted for 120 min, then a secondary antibody was added and reacted for 20 min, then a substrate solution was added and reacted for 20 min in sequence, and then the absorbance of the mixed solution was detected by a spectrophotometer. The experimental result is as shown in FIG. 8B, the transverse axis in FIG. 8B represents the amount of added TNF-α, and the longitudinal axis represents the detected absorbance. As shown in FIGS. 8A and 8B, the capability of the liposome for detecting the protein concentration is similar to that of the commercial fluorescence immunoassay kit. Therefore, it can be known from the experiment that, the adsorption capability of the liposome to protein can be applied in detection of protein concentration.

EXPERIMENTAL EXAMPLE 8

In this experiment, whether the liposome has the capability of carrying drugs is observed by MTT assay. First, curcumin was added into cells at different concentrations, to obtain the curcumin concentration required for killing 50% of the cells. The experiment result is as shown in Table 1. Next, the liposome with curcumin at different concentrations (curcumin-liposome) was sent into cells of the same type respectively, to obtain the curcumin concentration required for killing 50% of the cells. The experiment result is as shown in Table 1. In Table 1, all the concentrations are expressed as mean±standard deviation (SD) (n=6).

TABLE 1

| Cell Line | Cancer Type | Curcumin (μmol/L) | Curcumin-liposome (10:3:3) (μmol/L) | Curcumin-liposome (10:1:1) (μmol/L) |
|---|---|---|---|---|
| Mouse | | | | |
| B16/F10 | Melanoma | 8.16 ± 1.01 | 1.10 ± 0.05 | 1.01 ± 0.06 |
| LL-2 | Lung carcinoma | 10.84 ± 2.33 | 1.41 ± 0.23 | 1.48 ± 0.12 |
| CT-26 | Colorectal adenocarcinoma | 7.92 ± 0.77 | 1.22 ± 0.05 | 1.60 ± 0.19 |
| JC | Breast adenocarcinoma | 11.03 ± 1.47 | 1.26 ± 0.07 | 1.47 ± 0.19 |
| Human | | | | |
| HepG2 | Hepatocellular carcinoma | 12.21 ± 1.11 | 1.67 ± 0.16 | 1.64 ± 0.15 |
| A549 | Lung carcinoma | 30.01 ± 9.45 | 1.37 ± 0.06 | 1.41 ± 0.04 |
| HT-29 | Colorectal adenocarcinoma | 12.89 ± 1.18 | 1.53 ± 0.05 | 1.44 ± 0.15 |
| HeLa | Cervical cancer | 17.66 ± 6.95 | 1.19 ± 0.17 | 1.18 ± 0.13 |

The ratio of the neutral lipid membrane, the positively charged polymer, and the surface active polymer in the liposome is 10:3:3 and 10:1:1 respectively. It can be known from Table 1 that, the curcumin encapsulated in the liposome has cytotoxic effect on the cells at a low concentration. That is to say, the liposome has the capability of carrying drugs and releasing drugs, and the liposome can effectively improve the effect of the carried drugs.

EXPERIMENTAL EXAMPLE 9

Figure 9:
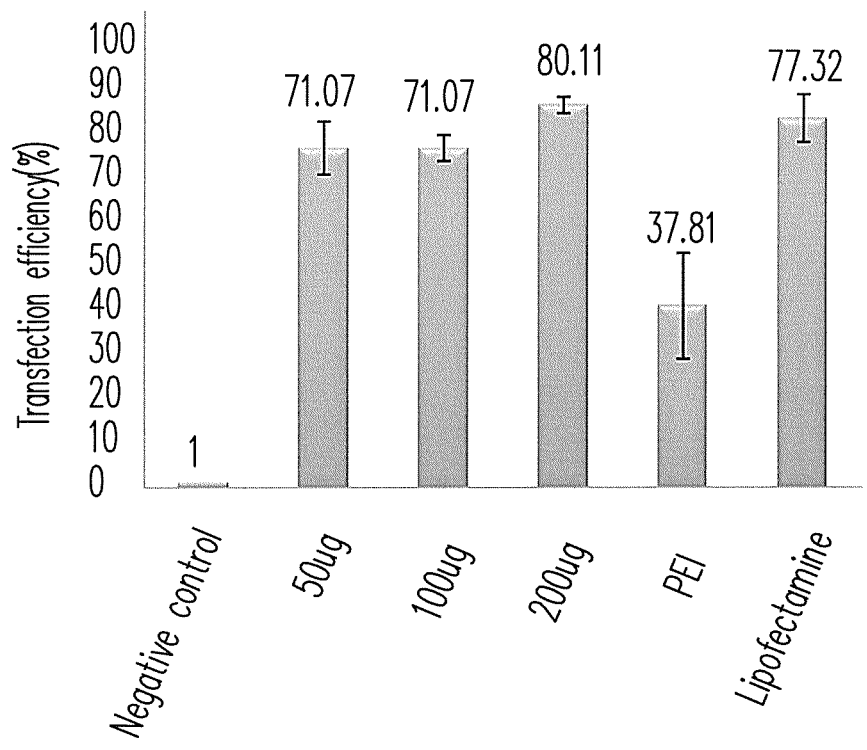
FIG. 9 shows experimental result of transfecting AAV-MCS-hrGFP into Balb/3T3 cell with different transfection reagents.

In this experiment, whether the liposome has excellent transfection efficiency is observed. Particularly, 50 μg, 100 μg, 200 μg liposome and PEI were added into a transfection reagent respectively, and AAV-MCS-hrGFP was transfected into Balb/3T3 cell by the transfection reagent. Next, the transfected Balb/3T3 cell was analyzed by a flow cytometer. The experimental result is as shown in FIG. 9. Further, in a positive control, AAV-MCS-hrGFP was transfected into Balb/3T3 cell by a Lipofectamine transfection reagent, and negative control was untransfected Balb/3T3 cell and AAV-MCS-hrGFP, and the Balb/3T3 cell was analyzed by a flow cytometer. The experimental result is as shown in FIG. 9. The transverse axis in FIG. 9 represents different transfection reagents, and the longitudinal axis represents the percentage of transfected Balb/3T3 cell expressing green fluorescent protein (GFP) measured by the flow cytometer, in which the percentage of the cell expressing GFP is indicative of the transfection efficiency. As shown in FIG. 9, the liposome has excellent transfection efficiency, which is significantly higher than that of the PEI carrier and is similar to that of the commercial Lipofectamine transfection reagent. Therefore, the liposome can be applied in cell transfection.

In view of the above, the liposome of the present invention has the following advantages:

The liposome of the present invention is based on the neutral lipid membrane, and the positively charged polymer and the surface active polymer are dispersed on the neutral lipid membrane by non-covalent bonding.

The liposome of the present invention adsorbs a material by non-covalent bonding, thus avoiding the influence or damage to the activity or configuration of the adsorbed material.

The liposome and the liposome composition of the present invention have the property of being capable of being centrifuged, thus facilitating purification thereof.

The liposome of the present invention has the properties of being capable of encapsulating drugs and performing cell transfection.

The liposome of the present invention can rapidly and stably adsorb a material, such as protein, nucleic acid, and targeting molecule to form a liposome composition, thus the liposome composition can be used as probe to perform specific identification and analysis on protein, nucleic acid, or cell.

The liposome of the present invention can encapsulate a biologically active material and adsorb a targeting molecule, thus the formed liposome composition has cell specificity, tissue specificity, or tumor specificity, thereby significantly improving the transfection efficiency of the liposome composition or the therapy effect of drugs.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A liposome, comprising:
    a neutral lipid membrane, formed as a hollow sphere;
    a positively charged polymer, dispersed on the neutral lipid membrane by non-covalent bonding; and
    a surface active polymer, dispersed on the neutral lipid membrane by non-covalent bonding, wherein the positively charged polymer and the surface active polymer are not covalently bonded.

2. The liposome according to claim 1, wherein the ratio of the neutral lipid membrane, the positively charged polymer, and the surface active polymer ranges from 5:2:2 to 60:1:1, wherein the positively charged polymer: the surface active polymer is 1:1.

3. The liposome according to claim 2, wherein the ratio of the neutral lipid membrane, the positively charged polymer, and the surface active polymer ranges from 5:2:2 to 30:1:1.

4. The liposome according to claim 3, wherein the ratio of the neutral lipid membrane, the positively charged polymer, and the surface active polymer is 3:1:1.

5. The liposome according to claim 1, wherein the neutral lipid membrane is selected from a group consisting of DLPC, DOPC, DMPC, DPPC, DSPC, DOPC, DMPE, DPPE, DOPE, DMPA, DPPA, DOPA, DMPG, DPPG, DOPG, DMPS, DPPS, and DOPS.

6. The liposome according to claim 5, wherein the neutral lipid membrane includes DLPC and DOPC.

7. The liposome according to claim 1, wherein the positively charged polymer is selected from a group consisting of polyamine, polyethyleneimine (PEI), polyvinylpyrrolidone, and polylactic acid.

8. The liposome according to claim 7, wherein the positively charged polymer is PEI.

9. The liposome according to claim 1, wherein the surface active polymer is selected from a group consisting of crosslinked polyacrylate, saponin, and polyethylene glycol.

10. The liposome according to claim 9, wherein the surface active polymer is polyethylene glycol.

11. The liposome according to claim 1, wherein the neutral lipid membrane is fluorescent.

12. The liposome according to claim 1, wherein the liposome encapsulates a biologically active material.

13. The liposome according to claim 12, wherein the biologically active material is selected from a group consisting of virus, protein, peptide, nucleic acid, polysaccharide, carbohydrate, lipid, glycoprotein, and pharmaceutical ingredients.

14. The liposome according to claim 1, further comprising a material adsorbed by non-covalent bonding, and the bound material is irreplaceable by excess same materials in solution.

15. The liposome according to claim 14, wherein the material is protein.

16. The liposome according to claim 14, wherein the material is nucleic acid.

17. The liposome according to claim 16, wherein the material is deoxyribonucleic acid (DNA).

18. The liposome according to claim 16, wherein the material is ribonucleic acid (RNA).

19. The liposome according to claim 14, wherein the material is targeting molecule.

20. The liposome according to claim 19, wherein the material is antibody.

21. The liposome according to claim 19, wherein the material is cytokine.

22. The liposome according to claim 19, wherein the material is peptide.

23. The liposome according to claim 14, wherein the neutral lipid membrane is fluorescent.

24. The liposome according to claim 14, wherein the neutral lipid membrane encapsulates a biologically active material.

25. The liposome according to claim 24, wherein the biologically active material selected from a group consisting of virus, protein, peptide, nucleic acid, polysaccharide, carbohydrate, lipid, glycoprotein, and pharmaceutical ingredients.

26. A method for producing a liposome, comprising:
    forming a neutral lipid membrane in a vessel;
    adding a positively charged polymer solution and a surface active polymer solution into the vessel; and
    shaking the vessel.

27. The method for producing a liposome according to claim 26, wherein the step of shaking the vessel makes the neutral lipid membrane formed as a hollow sphere, and the positively charged polymer and the surface active polymer dispersed on the neutral lipid membrane by non-covalent bonding.

28. The method for producing a liposome according to claim 27, wherein the non-covalent bonding comprises hydrophilic and hydrophobic force, electrostatic force, hydrogen bond or van der waals force.

29. The method for producing a liposome according to claim 26, wherein the ratio of the neutral lipid membrane, the positively charged polymer, and the surface active polymer ranges from 5:2:2 to 60:1:1.

30. The method for producing a liposome according to claim 29, wherein the ratio of the neutral lipid membrane, the positively charged polymer, and the surface active polymer ranges from 5:2:2 to 30:1:1.

31. The method for producing a liposome according to claim 30, wherein the ratio of the neutral lipid membrane, the positively charged polymer, and the surface active polymer is 3:1:1.

32. The method for producing a liposome according to claim 26, wherein the neutral lipid membrane is selected from a group consisting of DLPC, DOPC, DMPC, DPPC, DSPC, DOPC, DMPE, DPPE, DOPE, DMPA, DPPA, DOPA, DMPG, DPPG, DOPG, DMPS, DPPS, and DOPS.

33. The method for producing a liposome according to claim 32, wherein the neutral lipid membrane comprises DLPC and DOPC.

34. The method for producing a liposome according to claim 26, wherein the positively charged polymer is selected from a group consisting of polyamine, polyethyleneimine (PEI), polyvinylpyrrolidone, and polylactic acid.

35. The method for producing a liposome according to claim 34, wherein the positively charged polymer is PEI.

36. The method for producing a liposome according to claim 26, wherein the surface active polymer is selected from a group consisting of crosslinked polyacrylate, saponin, and polyethylene glycol.

37. The method for producing a liposome according to claim 36, wherein the surface active polymer is polyethylene glycol.

38. The method for producing a liposome according to claim 26, wherein the formation method of the neutral lipid membrane comprises:
    adding a neutral lipid solution into the vessel; and
    removing a solvent from the neutral lipid solution, to form a multi-layer neutral lipid membrane at the bottom of the vessel.

39. The method for producing a liposome according to claim 26, wherein the neutral lipid membrane is fluorescent.

40. The method for producing a liposome according to claim 26, further comprising passing the formed liposome through a pore membrane.

41. The method for producing a liposome according to claim 40, wherein the size of the pore membrane is 200 mn.

42. The liposome according to claim 1, wherein the positively charged polymer is PEI, the surface active polymer is polyethylene glycol, and the positively charged polymer: the surface active polymer is 1:1.

* * * * *